United States Patent [19]

Workman et al.

[11] 4,412,345

[45] Oct. 25, 1983

[54] APPARATUS AND METHOD FOR PRECISE DETERMINATIONS OF CRYSTALLOGRAPHIC ORIENTATION IN CRYSTALLINE SUBSTANCES

[75] Inventors: S. Thomas Workman, Saratoga; John L. Chambers, Sunnyvale; Myron A. Pugh, San Jose, all of Calif.; Roger W. Ward, Loveland, Colo.

[73] Assignee: The United States of America as represented by the Secretary of the Army, Washington, D.C.

[21] Appl. No.: 289,353

[22] Filed: Aug. 3, 1981

[51] Int. Cl.³ ............................................ G01N 23/20
[52] U.S. Cl. ..................................... 378/078; 356/31; 378/81
[58] Field of Search ...................... 378/81, 206, 78, 76; 356/31

[56] References Cited

U.S. PATENT DOCUMENTS 2,392,528  1/1946  Fankuchen ............................ 378/81
2,457,555 12/1948  Haworth ............................... 378/78
4,065,211 12/1977  Vig ....................................... 378/81

Primary Examiner—Alfred E. Smith
Assistant Examiner—T. N. Grigsby
Attorney, Agent, or Firm—Robert P. Gibson; Jeremiah G. Murray; John W. Redman

[57] ABSTRACT

An apparatus and method for precisely measuring the angles of cut of single and doubly rotated cuts of quartz crystal blanks on a high volume production basis.

5 Claims, 3 Drawing Figures

APPARATUS AND METHOD FOR PRECISE DETERMINATIONS OF CRYSTALLOGRAPHIC ORIENTATION IN CRYSTALLINE SUBSTANCES

GOVERNMENT LICENSE

The Government has rights in this invention pursuant to Contract No. DAAK20-79-0254 awarded by the Department of the Army.

BACKGROUND OF THE INVENTION

This invention relates generally to apparatus for measuring the crystallographic orientation (angle of cut) of already manufactured single crystal plates, such as quartz resonator plates, of singly and double rotated cuts. The angles of cut of double rotated plates can be described by the IEEE notation of (YXWl) $\phi/\theta$. This notation is explained in "Standards on Piezoelectric Crystals, 1949", Proc, IRE, Vol. 37, Dec. 1949, pp. 1378–1395, and in IEEE Standard No. 176 incorporated herein by reference. An SC-cut, for example, may be described as (YXWl) 22.43°/34.31°. For simplicity, a cut may also be described by stating the two rotation angles only, e.g. $\phi=22.43°$, $\theta=34.31°$ describes the same SC-cut. Orientation in the plane of the plate shall be denoted by $\psi$, which is an angle measured from the X"-axis. Definitions of the various cuts can be found in the references. For purposes of these guidelines, the AT and SC-cuts shall be defined as the $\phi=0.0°\pm0.4°$ and $\phi=22.0°\pm0.8°$ cuts respectively on the $\phi>0$ branch of the bulk wave zero temperature coefficient locus.

For the case of singly rotated cuts, such as the AT-cut, automated single axis, double crystal X-ray diffractometers are readily available with sufficient accuracy to attain high manufacturing yield. Details of one such system are described in U.S. Pat. No. 4,065,211. However, a practical apparatus to determine the angle of cut of "doubly rotated" cuts, such as the SC-cut, has not been available prior to this invention. Such a device employing a monochromatic X-ray source would require a complex goniometer with at least three axes of rotation.

Double rotated quartz crystal resonators, particularly the SC-cut have been shown to have smaller frequency shifts induced by mechanical stresses in the plane of the resonator than the single rotated AT-cut resonators. These cuts have also been shown to be less sensitive to the thermal stresses produced by sudden temperature changes. Doubly rotated quartz cuts, therefore, have the potential for providing resonators of superior stability with respect to vibration, oven temperature fluctuations, temperature cycling (in ovenless applications), and time. (e.g., long term aging). To produce doubly rotated blanks, two angles must be specified and controlled to a high degree of accuracy during the manufacturing process. Therefore if the superior qualities of the SC-cut are to be realized on a large scale, there need be, as a minimum, crystal plate orientation and measurement apparatus with adequate throughput capability and sufficient accuracy to permit high yield manufacture.

SUMMARY

The X-ray apparatus of the present invention, termed a laser-assisted Laue Diffractometer is capable of determining the angles of cut for both singly and doubly-rotated single crystal plates to an accuracy of a few arc-seconds and at production rates consistant with industry norms. Other advantages include the capability of measuring single crystal blanks of various materials, i.e., quartz, silicon, cadmium telluride, etc., at any crystallographic orientation on the same apparatus. It is of simple design requiring only one degree of freedom for the single crystal balnk during measurement. It provides ease of complete automation due to simple geometry and large open volume above the crystal blank measuring station. Further, it employs a laser to measure the position of the front surface of the crystal blank thus eliminating inaccuracies caused by dirt particles and other debris that might be present between the crystal blank holding chuck and the rear surface of the blank. Lastly, it is capable of providing a permanent record to accompany each measured blank indicative of its quality and expected performance.

The apparatus of this invention is based on the Laue Diffraction method of crystalline analysis. The charcteristic feature of the Laue Diffraction method is the use of a continuous spectrum X-ray source rather than a monochromatic source. The fundamental advantage of the continuous spectrum is that the position of a Bragg reflection (i.e., diffraction maximum) varies in a continuous manner as the crystal orientation is changed with respect to the incident X-ray beam, whereas with monochromatic radiation, the reflection disappears as the crystal is rotated out of the Bragg condition. Thus reflections are more easily found in the Laue case which allows for a simpler diffractometer geometry and greater ease of automation than is possible for conventional monochromatic techniques. For example, using a doubly-rotated plate, such as the SC-cut, and knowning its $\phi$ and $\theta$ orientations to 30 min of arc, only a single rotation of the blank about its face (i.e., completely about $\psi$) is necessary to position a Laue reflection in a detector. To completely determine the physical angles of orientation of the plate ($\phi$, $\theta$, $\psi$), X, Y, and Z coordinates for a minimum of two reflections are necessary. These two reflections can be chosen such that they are the only pair which will enter two detectors simultaneously during a full rotation about $\psi$. The determination of the spot coordinates thus proceeds in two stages. First, the blank is rotated about $\psi$ until the two reflections simultaneously enter two appropriately prepositioned area detectors. Second, the position of each reflection spot is precisely determined by scanning both detectors either electrically or with precision mechanically driven apertures in two dimensions and computing the coordinates of each spot center by least-squares fit of a model spot profile. Since the orientation of the Laue pattern with respect to the face of the plate must be computed, the orientation of the face is measured with a reflected laser beam and a position-sensitive photo diode detector. The degree of precession of the laser beam reflected from the face of the blank as it is rotated about $\psi$ is used to compute the face orientation. Since the accuracy of the orientation must be on the order of seconds of arc, sensitivity of the Laue spot positions to the crystal orientation is of prime concern. The diffraction vectors of the two reflections used for orientation should be chosen to insure maximum sensitivity to both $\phi$ and $\theta$.

The suitability of using the Laue reflections for orientation depends on a number of factors. First, they must be of high intensity, since the time required for measurement depends inversely on the counting rate. To obtain high intensity, the diffracted energy (or energies)

should correspond to an energy region of high source intensity. Second, the reflections should be sensitive to the crystal orientation, as discussed above (e.g. the diffraction vectors should be as close to 90° apart as possible). The third criterion is that the reflections permit an unambiguous initial positioning of the crystal about $\psi$.

A computer program was written to enable prediction of the diffraction patterns which would be observed for the various cuts, and identification of pairs of reflections suitable for orientation. The Laue pattern prediction program works with arbitrary diffraction geometries enabling prediction of patterns and motion of the spots, and selection of suitable reflections for measurement in the glancing angle mode. The sensitivities of $\phi$, $\theta$, $\psi$ to variations in the measured data were computed, and a least-squares algorithm developed to determine $\phi$, $\theta$, $\psi$ given the observed positions of two Laue spots. A least-squares algorithm for determination of the orientation of the face of the blank from the motion of a laser beam reflected from its surface as it rotates was also developed.

DETAILED DESCRIPTION OF THE DRAWINGS

Figure 1:
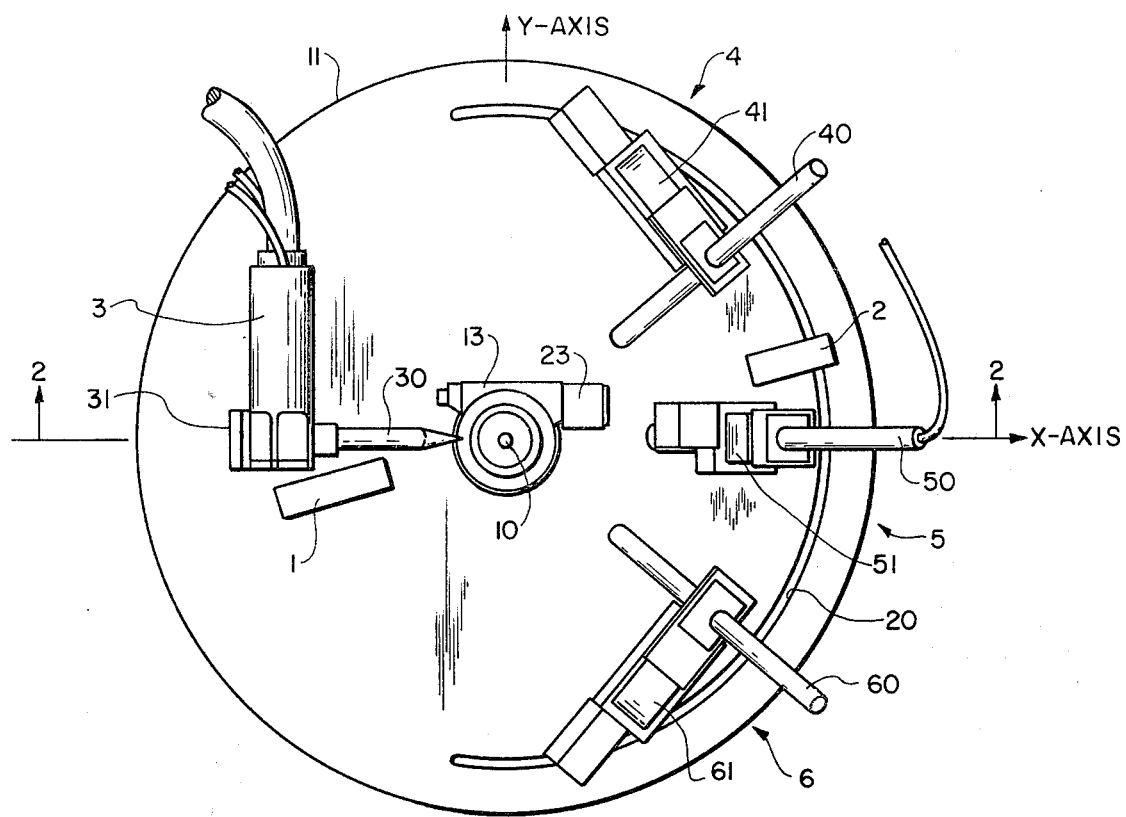
FIG. 1 is a plan view of the Laue Diffractometer utilizing three position sensitive X-ray area detectors.

FIG. 1 depicts an illustrative Laue Diffractometer 100. As shown, the Diffractometer comprises a laser 1 and laser photodiode detector 2 for ascertaining the face angle of a crystal 10 to be measured upon rotaty table 13. X-ray tube 3 is a tungsten-target continuous-spectrum X-ray source. Collimator 30 is fixedly mounted to table 11 for illuminating a crystal 10 to be placed on rotary table 13. Shown at 23 is a precision continuous stepper motor for turning the rotary table 13. Detector assemblies 4, 5 and 6 are adjustable mounted on table 11. Detector adjust slot 20 is provided to allow dector assemblies 4 and 6 to be prepositioned with respect to X-ray source 3 in accordance with the particular type of crystal and cut to be measured. Automated motor means, not shown, may be provided for this purpose. In the arrangement shown, each of these Detector assemblies 4 and 6 is movable through approximately 80°. The Detector assemblies 4, 5 and 6 comprise Detectors 40, 50 and 60 and Translation stages 41, 51 and 61.

Figure 2:
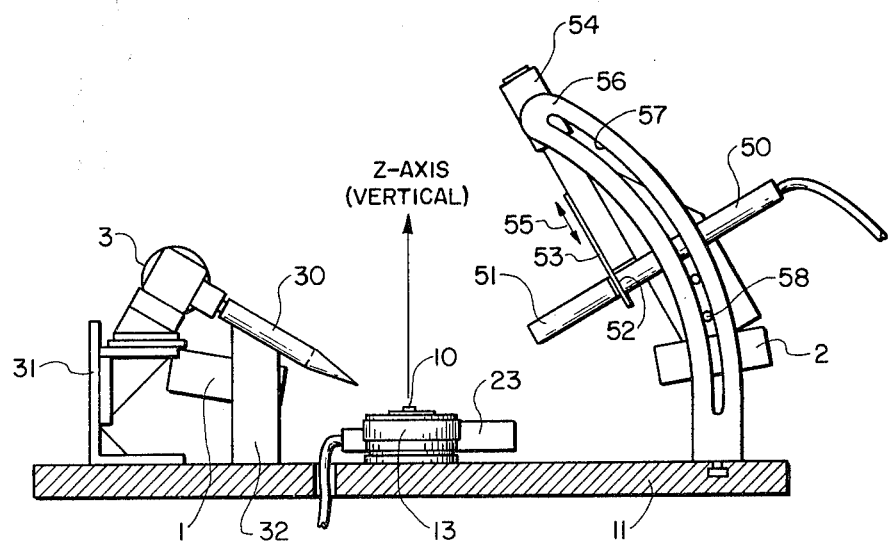
FIG. 2 is a sectional view along 2—2 of FIG. 1.

FIG. 2 is a view along lines 2—2 of FIG. 1. In this view can be seen the X-ray tube mounting stage 31 and collimator mount 32. Detector assembly 5 is shown in its various parts. X-rays diffracted by crystal 10 pass through Detector Collimator 51 through single axis slit 53, Detector aperture 52 and into Detector 50. Single axis split 53 is controlled by translation stage 54. Arrow 55 shows the direction of slit motion. Analagous to slot 20 on table 11 for the adjustment of Detector assemblies 4 and 6 is Detector mount 56 and Detector adjust slot 57. Vertical angle adjust 58 could be automated by motor means, not shown.

With the three detector assemblies 4, 5 and 6 shown, movable through the angles shown, any two of these detectors may be positioned to receive chosen diffracted reflections.

Figure 3:
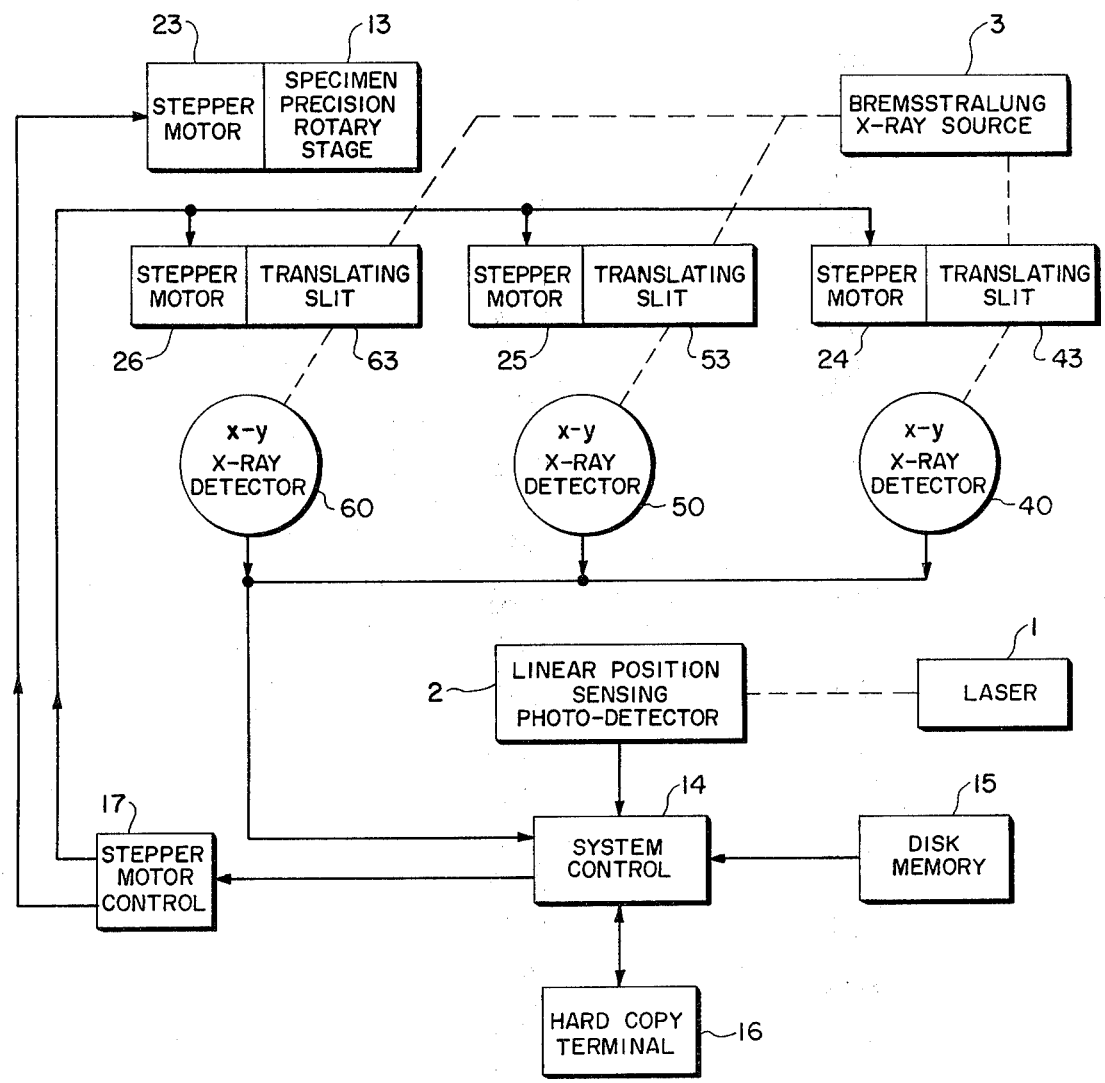
FIG. 3 is a block diagram of the control system of the preferred embodiment utilizing mechanically driven apertures.

FIG. 3 depicts in block diagram form the control system and major elements of the Laue Diffractometer. System control 14 receives control information from memory 15 and terminal 16 and through stepper motor control 17, and stepper motors 24, 25 and 26, precisely locate the positions of the diffracted reflections in at least two X-ray detectors. The position data along with the position of the plane of the face from the laser detector 2 is inputed to the system control which transforms its information into X, Y and Z coordinates for each reflection and determines the angle between the front surface and the crystalographic axis of the single crystal blank being measured. This information is outputed to a hard copy terminal 16 to make a permanent record for each crystal.

Having thus disclosed my invention, I claim:

1. An apparatus for determining the crystal angles of single crystal blanks comprising:
    rotating table means for mounting a single crystal blank whose angles are to be determined;
    surface plane measuring means for measuring the position of a surface of a single crystal blank mounted on said rotating table means;
    internal atomic planes measuring means comprising a continuous spectrum X-ray source means for illuminating a portion of the surface of the crystal blank to be measured and at least two position sensitive X-ray area detectors for simultaneously receiving at least a portion of the spectrum of said continuous spectrum X-ray source diffracted from said blank,
    integrated control means for controlling the rotation of said table mean, controlling said surface plane measuring means and controlling said atomic planes measuring means; and
    determining means for deriving depiction of the physical angles of a particular crystal blank from the measured angles of said surface plane ofsaid blank and said atomic planes of said blank.

2. The apparatus of claim 1 wherein said surface plane measuring means comprises a laser light source means for illuminating a portion of the surface of the crystal to be measured, a detector means for receiving a laser light beam reflected from said crystal comprising light sensing position means for detecting exact position of said light beam within said detector and measurement means for outputing movement of said light beam within said detectors as a measured angle.

3. A method of measuring the crystallographic orientation of single crystal plates of singly and doubly rotated cuts comprising the steps of;
    affixing a major surface of a crystal to be measured to a rotatable table;
    reflecting the output of a collimated light source from a small portion of a major surface of said crystal, measuring the degree of precession of said reflected light beam;
    reflecting from said small portion of said crystal the output of another source of collimated electromagnetic radiation capable of producing at least two diffracted reflections;
    measuring the angle of each of the diffracted reflections generated from said other source; and
    computing the angle of cut from the measured angles.

4. A method of measuring the crystallographic orientation of single crystal plates of singly and doubly rotated cuts comprising the steps of:

affixing a major surface of a crystal to be measured to a rotatable table;

reflecting from a major surface of said crystal the output of a collimated light source;

measuring the degree of precession of said reflected light beam;

reflecting from said small portion of said crystal the output of another source of collimated Electro-Magnetic radiation capable of producing at least two diffracted reflections;

choosing a pair of expected diffracted reflections from said crystal with an angular spacing of approximately 90° between normals to the sets of diffracting planes;

positioning one or more area detectors capable of receiving the output of said other source in an area which will receive only said expected diffracted reflections;

stopping rotation of said table when said expected reflections simultaneously enter said area detectors;

measuring the angles of each of said diffracted reflections; and computing the angle of cut from the measured angles.

5. The method of claim 3 or 4 wherein the angles of the diffracted reflections are determined by computing the coordinates of each diffracted reflection by least-squares fit of a model reflection profile.

* * * * *